United States Patent [19]

Umezawa et al.

[11] Patent Number: 4,658,058

[45] Date of Patent: Apr. 14, 1987

[54] 11-O-METHYLSPERGUALIN

[75] Inventors: Hamao Umezawa; Tomio Takeuchi, both of Tokyo; Shinichi Kondo, Yokohama; Hironobu Iinuma; Daishiro Ikeda, both of Tokyo; Teruya Nakamura, Kusatsu; Akio Fujii, Kamakura, all of Japan

[73] Assignee: Zaidan Hojin Biseibutsu Kagaku Kenkyu Kai, Tokyo, Japan

[21] Appl. No.: 723,169

[22] Filed: Apr. 15, 1985

Related U.S. Application Data

[63] Continuation-in-part of Ser. No. 426,372, Sep. 29, 1982, Pat. No. 4,518,532.

[30] Foreign Application Priority Data

Oct. 8, 1981 [JP] Japan .................................. 56-159503

[51] Int. Cl.⁴ .......................................... C07C 103/07
[52] U.S. Cl. .................................................. 564/159
[58] Field of Search ................................ 564/157, 159; 260/404.5 PA, 404.5 G, 112.5 R

[56] References Cited

U.S. PATENT DOCUMENTS 4,416,899 11/1983 Umezawa et al. .................. 424/320

| | | | |
|---|---|---|---|
| 4,430,346 | 2/1984 | Umezawa et al. | 564/159 X |
| 4,518,532 | 5/1985 | Umezawa et al. | 260/404.5 |
| 4,518,802 | 5/1985 | Umezawa et al. | 564/201 |
| 4,525,299 | 6/1985 | Umezawa et al. | 260/112.5 R |
| 4,529,549 | 7/1985 | Umezawa et al. | 260/404.5 R |

FOREIGN PATENT DOCUMENTS 2084999 4/1982 United Kingdom .

OTHER PUBLICATIONS

Shoji et al., Jour. of Antibiotics 29, 390–393 (1976).
Kido et al., *ibid.* 33, 791–795 (1980).
Takeuchi et al., ibid. 34, 1619–21 (1981).
Umezawa et al., ibid. 34, 1622–24 (1981).
Kondo et al., ibid. 34, 1625–27 (1981).
Kondo et al., Abstracts International Conference on Trends in Antibiotic Research, Tokyo Jun. 14, 15, 1982—p. 15.

*Primary Examiner*—Charles F. Warren
*Assistant Examiner*—Elizabeth A. Flaherty
*Attorney, Agent, or Firm*—Robert E. Carnahan

[57] ABSTRACT

The novel compound N-[(3-aminoproypl)aminobutyl]-Z-(F-guandino-3-hydroxyheptanamido)-2-methoxyethanamide or a pharmaceutically acceptable salt thereof which has antitumor activity in experimental animals.

3 Claims, No Drawings

11-O-METHYLSPERGUALIN

CROSS-REFERENCE TO RELATED APPLICATION

This application is a continuation-in-part of U.S. application Ser. No. 426,372 filed Sept. 29, 1982 and now U.S. Pat. No. 4,518,532 patented May 21, 1985. The entire specification of Ser. No. 426,372 now U.S. Pat. No. 4,518,532 is incorporated herein by reference.

FIELD OF THE INVENTION

This invention is concerned with fatty acid amide derivatives of the polynitrogen containing type (Class 260, Subclass 404.5). It is also concerned with pharmaceutical compositions adapted for parenteral administration containing this substance. The compound with which this invention is concerned is an active antitumor substance with respect to experimental animal tumors.

BACKGROUND OF THE INVENTION

Spergualin is an antitumor substance discovered by Umezawa et al., Journal of Antibiotics, 34, 1619–1621 (1981); Umezawa et al., ibid., 34, 1622–1627 (1981); and Umezawa et al., U.S. Pat. No. 4,416,899 patented Nov. 22, 1983.

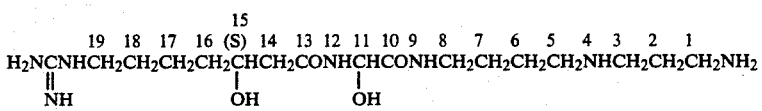

The configuration at the position 15 is S, while that at the position 11 is yet to be determined [Journal of Antibiotics, Vol. 34, 1622 (1981)]. The compound of this formula is synthesized by the condensation of the acid amide and glyoxylylspermidine (Umezawa et al. U.S. Pat. Nos. 4,518,802 and 4,430,346 patented May 21, 1985 and Feb. 7, 1984 respectively). The resulting epimeric compound is resolved into natural (−)-spergualin and non-natural (+)-spergualin [Journal of Antibiotics, Vol. 34, 1625 (1981)].

SUMMARY OF THE INVENTION

The present invention is concerned with the 11-O-methyl derivative of spergualin. This compound has the structure shown above with respect to spergualin except that the 11—OH group is replaced by an 11—OCH$_3$ group. The racemic form with respect to position-11 and each of the epimers thereof are included in the present invention.

The present substance exhibits a capacity for inhibiting experimental animal tumors which is equivalent to that of spergualin, although the potency thereof on a weight basis is less. The lower potency is, however, compensated by a reduction in toxicity providing the substance with an overall favorable degree of antitumor activity.

Referring to the Umezawa et al. patent U.S. Pat. No. 4,416,899, spergualin in the free form is unstable. Refer to column 9, line 11. While the hydrochloride salt is stable, it is extremely hygroscopic. Refer to column 9, line 15. Although this is the preferred form for pharmaceutical purposes (column 14, line 5), the extreme hygroscopicity creates many inconveniences from the manufacturing standpoint. Further investigation of spergualin has also revealed that aqueous solutions thereof having pH values in excess of 4 are quite unstable.

The present substance overcomes the foregoing disadvantages displayed by spergualin in that the substance shows excellent stability in aqueous solutions within the range of pH 4–8. The present invention, therefore, includes not only the substance per se, but also pharmaceutical compositions adapted for antitumor use and comprising a solution of the compound in a pharmaceutically acceptable injection vehicle having pH 4–8 and preferably pH 6–8. The range pH 4–8 is critical with respect to parenteral injection in that intramuscular injection of a solution having a pH of less than 4 is quite painful. Solutions having lower pH values may be used intravenously, but it is preferred to operate within the range of pH 4–8 and preferably pH 6–8 for the comfort of the patient and with regard to the stability of the drug since the blood exhibits a pH of about pH 7.5.

DETAILED DESCRIPTION OF THE INVENTION

[I] Stability Test (a) Methods: The test compounds were dissolved in water and the solutions were adjusted to pH 2–10. The resulting solutions were heated to 60° C. and kept at the same temperature for 4 hours. The retention was determined by means of high performance liquid chromatography (HPLC). The column was packed with Nucleosil ® 5C$_{18}$. The solvent used for spergualin was a mixture (6:94) of acetonitrile—0.01M sodium pentanesulfonate+0.01M Na$_2$HPO$_4$ (pH 3), while that for the compound No. 22 of this invention was a mixture (7:93) of acetonitrile—0.005M sodium pentanesulfonate+0.01M Na$_2$HPO$_4$ (pH 3).

TABLE 1

| | Stability [Retention (%)] | | | | | | | | |
|---|---|---|---|---|---|---|---|---|---|
| | Compound | | | | | | | | |
| pH | 2 | 3 | 4 | 5 | 6 | 7 | 8 | 9 | 10 |
| No. 22 | | | | | | | | | |
| (−) | 79.7 | — | 100 | 100 | 100 | 100 | 100 | 97.6 | 95.7 |
| (±) | 79.7 | — | 100 | 100 | 100 | 100 | 100 | 100 | 95.6 |
| (−)-spergualin | 88.1 | 88.0 | 87.8 | 82.5 | 46.5 | 12.6 | 6.1 | 0 | — |

[II] Therapeutic Effect on Implanted Cancer in Mice (a) Methods:

BDF$_1$ strain male mice (5 weeks old) were each inoculated intraperitoneally with 10$^5$ mouse leukemia L-1210 cells and treated once a day by intraperitoneal injection with a test compound dissolved in physiological saline for 6 consecutive days beginning from the day of inoculation. The mice were then observed for 30 days to determine the rate of prolongation of survival period=100×T/C=100×(average survival days of treated group)/(average survival days of control group). The therapeutic effects of typical compounds of this invention on mouse leukemia L-1210 were as shown in Table 2.

(b) Results:

TABLE 2

Treatment of Murine Leukemia L-1210

| Compound | Dosage (mg/kg/day) | Prolongation of survival period (%), T/C (%) | Number of mice survived for 30 days |
| --- | --- | --- | --- |
| No. 22 | 50 | 7 | 0/8 |
| (±)-15S | 25 | >414 | 6/8 |
|  | 12.5 | >380 | 5/8 |
|  | 6.25 | >332 | 4/8 |
|  | 3.13 | 163 | 0/8 |
|  | 1.56 | 117 | 0/8 |
| No. 22 | 25 | >423 | 5/5 |
| (−)-15S | 12.5 | >408 | 4/5 |
|  | 6.25 | >400 | 4/5 |
|  | 3.13 | >290 | 1/5 |
|  | 1.56 | 177 | 0/5 |
| Spergualin | 100 | 0 | 0/4 |
|  | 50 | >333 | 1/4 |
|  | 25 | >372 | 2/4 |
|  | 12.5 | >386 | 2/4 |
|  | 6.25 | >401 | 3/4 |
|  | 3.13 | >340 | 2/4 |
|  | 1.56 | >229 | 1/4 |
|  | 0.78 | 136 | 0/4 |
|  | 0.39 | 104 | 0/4 |

In the foregoing material the compound of the present invention is referred to as No. 22. This designation derives from the parent application where the substance is described in Example 22. For convenience Examples 22, and 27 of the parent application are copied below. It is evident from Table 1 that the present substance is far superior to spergualin with respect to chemical stability in aqueous solution at pH 6–10. The percent retentions of Compound No. 22 in aqueous solution within that pH range are 95.6–100% while those of spergualin are only 0–46.5%.

To facilitate interpretation of the data given in Table 2, certain of that data have been extracted and formulated in Table 3 which follows. In Table 3 the maximal antitumor effect as represented by the maximal percent T/C and the dose at which that effect was achieved are tabulated. Also included in the table is the minimal effective dose. A minimal effect is regarded as a percent T/C of 125. The comparative toxicities of spergualin and Compound No. 22 are reflected in the right-hand column of Table 3 where the number of survivors for 30 days are indicated. The fractions given represent the number of survivors in the numerator and the number of animals in the test group in the denominator. Two values are given with respect to each line of data. The first refers to the number of survivors at the maximal effective dose and the second to the number of survivors at the minimal effective dose. The maximal effective dose for the racemic mixture of Compound No. 22 and for the pure (−) isomer of Compound No. 22 was 25 mg per kg of body weight, while that of spergualin was 6.25 mg per kg of body weight. The antitumor effect as represented by percent T/C was substantially equivalent for all three compounds, the value in each instance being in excess of 400%. A relatively low degree of toxicity in each instance is reflected by the number of survivors indicated in the last column. In the test with the pure (−) epimer of Compound No. 22, all animals survived the test. At the minimal effective doses none of the animals survived the 30 day test period.

TABLE 3

L-1210 Data Interpretation

| | Maximal T/C (%) | Effect Dose | Minimal Effective Dose | Number of Survivors for 30 days |
| --- | --- | --- | --- | --- |
| No. 22(±)-15S | >414 | 25 | 3.13 | 6/8; 0/8 |
| No. 22(−)-15S | >423 | 25 | 1.56 | 5/5; 0/5 |
| Spergualin | >401 | 6.25 | 0.78 | 3/4; 0/4 |

DESCRIPTION OF SPECIFIC EMBODIMENTS

Example 22

Synthesis of 11-O-methylspergualin

To a solution of 1.8 g (3.51 m moles) of (−)-spergualin trihydrochloride in 35 ml of anhydrous methanol was added 3.5 ml of 2N hydrogen chloride-methanol. The mixture was stirred at room temperature for 15 hours. The reaction mixture was evaporated to dryness, then dissolved in 30 ml of water, passed through a column of CM-Sephadex ® C-25 (Na-type; 600 ml) and fractionated by the gradient elution method with each 3 liters of water and 1M aqueous sodium chloride solution (fraction size, 17 g). fractions No. 208 to No. 230 were combined, evaporated to dryness and extracted three times with 10 ml of methanol. The methanol layer was passed through a column of Sephadex ® LH-20 (300 ml) and eluted with methanol to effect desalting (fraction size, 7 g). Fractions No. 19 to No. 33 were combined and evaporated to dryness to yield 1.528 g (82% yield) of a white powder of 11-O-methylspergualin trihydrochloride.

For the separation of 11-O-methylspergualin trihydrochloride into its epimeric components, use was made of HPLC on a column, 2 cm×25 cm, packed with Nucleosil ® 30C$_{18}$, a reversed phase packing material of M. Nagel Co. under the following conditions:

Flow rate: 10 ml/minute
Pressure: 30 kg/cm$^2$
Solvent: acetonitrile−[0.01M sodium pentanesulfonate+0.01M Na$_2$HPO$_4$ (pH 3)]=9:91
Charge: 6 mg
Detection: uv 205 nm In HPLC, the uv absorption peak for (−)-11-O-methylspergualin (retention time, 48.3 minutes) appeared first and that for (+)-11-O-methylspergualin (retention time, 56.5 minutes) followed. The fractionation was repeated 12 times. The fractions corresponding to each peak were collected and purified in a manner similar to that in Example 1 using CM-Sephadex ® C-25 (Na-type) and Sephadex ® LH-20 to obtain 32.9 mg of a white powder of (−)-11-O-methylspergualin trihydrochloride and 24.5 mg of a white powder of (+)-11-O-methylspergualin trihydrochloride.

Example 27

Synthesis of (−)-11-O-methylspergualin (a) (−)-1-N,4-bis(benzyloxycarbonyl)spergualin:

To a solution of 2.3 g (4.48 m moles) of (−)-spergualin trihydrochloride in a mixture of 11 ml of N,N-dimethylformamide and 11 ml of water, while being cooled in ice, was added 1.25 ml (8.96) m moles) of triethylamine followed by a solution of 2.24 g (8.97) m moles) of N-benzyloxycarbonyloxysuccinimide in 11 ml of N,N-dimethylformamide. The mixture was stirred for 15 hours at 5° C. The reaction mixture was concentrated under reduced pressure, dissolved in 10 ml of 0.5M aqueous sodium chloride solution, then passed through a column of Diaion ® HP-20 (400 ml) equilibriated with 0.5M aqueous sodium chloride solution, washed with 1 liter of 0.5M saline, then with 1 liter of water and eluted with methanol (fraction size, 15 g). Fractions No. 21 to No. 30 were combined and evaporated to dryness to yield 287 mg (82% yield) of a white powder of (−)-1-N,4-bis(benzyloxycarbonyl)spergualin hydrochloride; $[\alpha]_D^{21} -11°$ (c 1, water).

Proton NMR (in deuteromethanol), δ: 1.3–2.0 ($CH_2 \times 6$), 2.38 ($CH_2$), 2.9–3.4 ($NCH_2 \times 5$), 4.0 (CH), 5.04 ($CH_2$), 5.07 ($CH_2$), 5.56 (CH), 7.30 ($C_6H_5 \times 2$).

(b) (−)-1-N,4-bis(benzyloxycarbonyl)-11-O-methylspergualin:

To a solution of 78 mg (0.484 m mole) of he above (−)-1-N,4-bis(benzyloxycarbonyl)spergualin hydrochloride in 12 ml of methylene chloride, while being cooled in ice, was added 2.44 ml (0.484 m mole) of a solution of 0.1 ml of boron trifluoride-ether complex in 4 ml of methylene chloride. To the mixture was added portionwise 9 ml (1 ml at a time interval of 30 minutes to one hour) of a solution of diazomethane in methylene chloride. [The diazomethane solution was prepared by gradually adding 10 g of N-nitrosomethylurea to a mixture of 30 ml of a 40% potassium hydroxide solution and 100 ml of methylene chloride while cooling at 40° C. in water; separating the organic layer and extracting the aqueous layer with 10 ml of methylene chloride; combining the organic layers and drying over granular potassium hydroxide at 5° C. for 3 hours.] After 3.5 hours from the start of reaction, stirring was discontinued. After addition of several drops of dilute acetic acid, the reaction mixture was concentrated under reduced pressure, then dissolved in 3 ml of 50% aqueous methanol, passed through a column of Diaion ® HP-20 (100 ml), washed with 300 ml of 10% aqueous methanol and eluted with methanol (fraction size, 15 ml). Fractions No. 25 to No. 28 were combined and evaporated to dryness, yielding 262.4 mg of a white powder of a mixture of (−)-1-N,4-bis(benzyloxycarbonyl)-11-O-methylspergualin hydrochloride and unreacted (−)-1-N,4-bis(benzyloxycarbonyl)spergualin hydrochloride (recovery, 69.2% by weight). The composition of this mixture was determined by HPLC on a column of Nucleosil ® $5C_{18}$ (4.0×150 mm), eluted with a mixture (1:1) of acetonitrile and 0.01M $(NH_4)_2HPO_4$ at a flow rate of 0.8 ml/min. It was found that the ratio between (−)-1-N,4-bis(benzyloxycarbonyl)-11-O-methylspergualin hydrochloride (retention time, 10.47 minutes) and (−)-1-N,4-bis(benzyloxycarbonyl)spergualin hydrochloride (retention time, 7.74 minutes) was 47:50.

The above mixture (78.5 mg) was passed through a column of 30 ml of Silicagel ® 60 (Merck Co.) and eluted with 10% methanol-chloroform mixture. The eluate was purified by HPLC carried out under the same conditions as described above. Fractions showing uv absorption at 200 nm at a retention time of 28.6 mg of a white powder of (−)-1-N,4-bis(benzyloxycarbonyl)-11-O-methylspergualin hydrochloride; $[\alpha]_D^{25} -14.4°$ (c 1, methanol).

Proton NMR (in deuteromethanol), δ: 1.3–2.0 ($CH_2 \times 6$), 2.42 ($CH_2$), 2.9–3.4 ($NCH_2 \times 5$), 3.37 ($OCH_3$), 4.0 (CH), 5.03 ($CH_2$), 5.08 ($CH_2$), 5.34 (CH), 7.29 ($C_6H_5 \times 2$).

(c) (−)-11-O-methylspergaulin:

Into a mixture of 5 ml of ethanol, 5 ml of water and 0.36 ml of 1N-hydrochloric acid was dissolved 130 mg of the above mixture (47:50) of (−)-1-N,4-bis(benzyloxycarbonyl)-11-O-methylspergaulin hydrochloride and (−)-1-N,4-bis(benzyloxycarbonyl)spergualin hydrochloride. After addition of 50 mg of 10% palladium-carbon to the solution, the mixture was stirred under a hydrogen stream for 4 hours at room temperature. The catalyst was removed by filtration and the filtrate was evaporated to dryness. The residue was dissolved in 3 ml of water, passed through a column of 150 ml of CM-Sephadex ® C-25 (Na-type) and fractionated by the gradient elution method with each 900 ml of water and 1M aqueous sodium chloride solution (fraction size, 17 g). Fractions No. 76 to No. 81 were combined and desalted as in Example 22, using Sephadex ® LH-20 to obtain 25.4 mg (51% yield) of a white powder of (−)-11-O-methylspergaulin trihydrochloride; $[\alpha]_D^{25} -27.1°$ (c 1, water).

Fractions No. 83 to No. 86 of the eluate from the CM-Sephadex ® column were similarly desalted to recover 24.5 mg (52% recovery) of a white powder of (−)-spergaulin trihydrochloride.

Physical Data

| | Composition | | | | |
|---|---|---|---|---|---|
| Compound No. | Molecular Formula | | Elementary Analysis (%) | | |
| | | | C | H | N | Cl |
| 22 | $C_{18}H_{39}N_7O_4 \cdot 3HCl \cdot 3/2H_2O$ | Calcd. | 39.03 | 8.19 | 17.70 | 19.20 |
| | | Found | 39.03 | 8.50 | 17.49 | 19.15 |

| | Spectra | |
|---|---|---|
| Compound No. | Infrared Absorption Spectrum ($cm^{-1}$) | Proton-NMR Spectrum (δ value) |
| 22 | 3330, 2930, 1655, 1520, 1460, 1360, 1190, 1160, 1090, 1020 | 1.4–1.9 ($CH_2 \times 5$), 2.19 ($CH_2$), 2.49 ($CH_2$), 2.9–3.4 ($NCH_2 \times 5$), 3.41 ($CH_3$), 4.04 (CH), 5.35 (CH) |

| | Configuration | | |
|---|---|---|---|
| Compound No. | Position 15 | Position 11 | Specific Rotation $[\alpha]_D^{25}$ |
| 22 | (S) | (±) | 1.0° (c 1, $H_2O$) |
| | | (−) | −27.3° (c 1, $H_2O$) |
| | | (+) | +25.5° (c 1, $H_2O$) |

EXAMPLES OF PHARMACEUTICAL DOSAGE COMPOSITION AND INFORMATION ABOUT SALTS

By the examples shown above, 11-O-methylspergaulin are obtained as hydrochlorides. If other forms of salt are desired, the following procedure may be employed: the hydrochloride is dissolved in water, the resulting aqueous solution is passed through a strong basic ion exchange resin such as Amberlite ® IRA-400 or Dowex ® -1, the fractions containing the end compound are combined, and neutralized by the corresponding acid such as sulfonic acid, acetic acid or citric acid, an aqueous solution containing the same or its solution in a hydrophilic organic solvent such as methanol, ethanol, acetone, tetrahydrofuran or dioxane, and the neutralized solution is evaporated to dryness under vacuum. Any residual organic solvent is distilled off under vacuum, and the residue is freeze-dried. The salts corresponding to the acid are obtained, respectively.

EXAMPLE 28

Lyophilized Dosage Form

30 Parts by weight of 11-O-methylspergaulin hydrochloride obtained in Example 22 was dissolved in 2000 parts of purified water and filtered to make a germ free solution using Millipore filter-GS-type. The filtrate (1 ml) (about pH 5) was put into a vial of 10 ml capacity and lyophilized to yield a freeze-dried injection containing 30 mg of 11-O-methylspergualin hydrochloride.

EXAMPLE 29

Injectable Dosage Form

11-O-Methylspergualin hydrochloride, (10 g), 1 g of sodium citrate and 8 g of sodium chloride were dissolved in 1000 cc of purified water and the pH of the solution was adjusted to 6.5. Resultant solution was filtered to make a germ free solution using Millipore filter-GS-type. The filtrate (1 ml) was put into an ample.

What is claimed is:

1. N-[4-(3-aminopropyl)aminobutyl]-2-(7-guanidino-3-hydroxyheptanamido)-2-methoxyethanamide or a pharmaceutically acceptable salt thereof.

2. A pharmaceutically composition adapted for parenteral administration comprising a solution of a nontoxic anti-tumor effective amount of a compound of claim 1 in a pharmaceutically acceptable injection vehicle having pH 6-8.

3. The method for inhibiting an implanted murine tumor which comprises systemically administering to a mouse bearing L-1210 leukemia and a non-toxic anti-tumor effective amount of a compound of claim 1.

* * * * *